(12) United States Patent
Van Aalten et al.

(10) Patent No.: US 8,207,175 B2
(45) Date of Patent: Jun. 26, 2012

(54) INHIBITOR COMPOUNDS

(75) Inventors: Daniel Marinus Ferdinand Van Aalten, Dundee (GB); Ian Michael Eggleston, Bath (GB)

(73) Assignee: University Court of the University of Dundee (GB)

( * ) Notice: Subject to any disclaimer, the term of this patent is extended or adjusted under 35 U.S.C. 154(b) by 788 days.

(21) Appl. No.: 11/922,795

(22) PCT Filed: Jun. 21, 2006

(86) PCT No.: PCT/GB2006/002277
§ 371 (c)(1),
(2), (4) Date: Jan. 30, 2009

(87) PCT Pub. No.: WO2006/136822
PCT Pub. Date: Dec. 28, 2006

(65) Prior Publication Data
US 2009/0215798 A1 Aug. 27, 2009

(30) Foreign Application Priority Data

Jun. 21, 2005 (GB) .................................. 0512626.3
Aug. 31, 2005 (GB) .................................. 0517677.1

(51) Int. Cl.
C07D 519/00 (2006.01)
A61K 31/522 (2006.01)
A61P 11/06 (2006.01)
A61P 31/00 (2006.01)
A61P 37/08 (2006.01)

(52) U.S. Cl. ..................... 514/263.21; 544/271; 544/272

(58) Field of Classification Search .................. 544/271, 544/272; 514/263.21
See application file for complete search history.

(56) References Cited

FOREIGN PATENT DOCUMENTS

DE 290910 8/1914
JP 55167291 A * 12/1980

OTHER PUBLICATIONS

Kametani, et al, Yakugaku Zasshi (1980), 100(2), 192-9 (Abstract Only).*
Merz et al. "Purine derivatives. II. Bis theobromines", *Arch. Pharm* 297(3):146-157 (1964).
Sakuda et al. "The Structure of Allosamidin, A Novel Insect Chitinase Inhibitor, Produced by *Streptomyces* SP.", *Tetrahdron Letters* 27(22):2475-2478 (1986).
Notification of Transmittal of the International Search Report and the Written Opinion of the International Searching Authority, or the Declaration corresponding to International Application No. PCT/GB2006/002277 mailed Sep. 26, 2006.

* cited by examiner

*Primary Examiner* — Mark Berch
(74) *Attorney, Agent, or Firm* — Myers Bigel Sibley & Sajovec, PA

(57) ABSTRACT

The present invention relates to compounds and uses of compounds which interact with chitinase enzymes, in particular the inhibition of those enzymes. Compounds of the invention are generally depicted by the following formula:

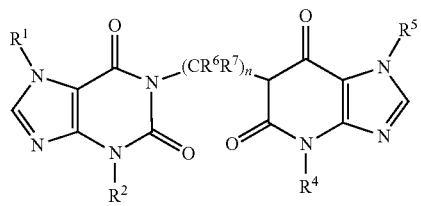

6 Claims, 1 Drawing Sheet

SEQUENCE LISTING

<160> NUMBER OF SEQ ID NOS: 4

<210> SEQ ID NO 1
<211> LENGTH: 36
<212> TYPE: DNA
<213> ORGANISM: Artificial
<220> FEATURE:
<223> OTHER INFORMATION: PCR primer

<400> SEQUENCE: 1
gccaccatgg tgcggtctgt ggcctgggca ggtttc        36

```
<210> SEQ ID NO 2
<211> LENGTH: 34
<212> TYPE: DNA
<213> ORGANISM: Artificial
<220> FEATURE:
<223> OTHER INFORMATION: PCR primer

<400> SEQUENCE: 2
tcaattccag gtgcagcatt tgcaggagtt gctg                              34

<210> SEQ ID NO 3
<211> LENGTH: 37
<212> TYPE: DNA
<213> ORGANISM: Artificial
<220> FEATURE:
<223> OTHER INFORMATION: PCR primer

<400> SEQUENCE: 3
gccaccatga caaagcttat tctcctcaca ggtcttg                           37

<210> SEQ ID NO 4
<211> LENGTH: 37
<212> TYPE: DNA
<213> ORGANISM: Artificial
<220> FEATURE:
<223> OTHER INFORMATION: PCR primer

<400> SEQUENCE: 4
ttatgcccag ttgcagcaat cacagctggt gtcgaag                           37
```

INHIBITOR COMPOUNDS

CROSS-REFERENCE TO RELATED APPLICATIONS

This application is a 35 U.S.C. §371 national phase application of PCT Application No. PCT/GB2006/002277, filed on Jun. 21, 2006, which claims priority from Great Britain Application Serial No. 0512626.3 filed on Jun. 21, 2005 and Great Britain Application Serial No. 0517677.1 filed on Aug. 31, 2005, the disclosures and contents of which are incorporated by reference herein in their entireties. The above-referenced PCT International Application was published in the English language as International Publication No. WO 2006/136822A1.

STATEMENT REGARDING ELECTRONIC FILING OF A SEQUENCE LISTING

A Sequence Listing in ASCII text format, submitted under 37 C.F.R. §1.821, entitled 9013-84_ST25.txt, 1,083 bytes in size, generated on Jan. 19, 2012 and filed via EFS-Web, is provided in lieu of a paper copy. This Sequence Listing is hereby incorporated by reference into the specification for its disclosures.

The present invention relates to compounds and uses of compounds which interact with chitinase enzymes, in particular inhibition of those enzymes.

BACKGROUND

Broadly, the present invention relates to inhibition of chitinases.

Family 18 chitinases are found in a range of pathogenic organisms and also play a role in the pathophysiology of inflammation, such as lung inflammation and asthma.

Chitin, a polymer of β(1,4) linked N-acetylglucosamine (GlcNAc), is an essential structural component of fungal cell walls, the shells of nematode eggs and arthropod exoskeletons. Family 18 chitinases, which degrade this polymer, have recently been chemically and/or genetically validated as potential drug targets against pathogenic fungi [M. J. Kuranda and P. W. Robbins, Chitinase is required for cell-separation during growth of *Saccharomyces cerevisiae, j. Biol. Chem.*, 266, 19758-19767 (1991); N. Takaya, D. Yamazaki, H. Horiuchi, A. Ohta, and M. Takagi, Cloning and characterisation or a chitinase-encoding gene chiA from *Aspergillus nidulans*, disruption of which decreases germination frequency and hyphal growth, *Biosci.Biotechno.Biochem.*, 62, 60-65 (1998); and S. Sakuda. Studies on the chitinase inhibitors, allosamidins, volume 2 of *Chitin Enzymology*, pages 203-212. Atec Edizioni, 1996], nematodes [K. Arnold, L. J. Brydon, L. H. Chappell, and G. W. Gooday, Chitinolytic activities in heligmosomoides-polygyrus and their role in egg hatching, *Mol.Biochem.Parasitol.*, 58, 317-323 (1993)], malaria transmission [J. M. Vinetz, J. G. Valenzuela, C. A. Specht, L. Aravind, R. C. Langer, J. M. C Ribeiro, and D. C. Kaslow, Chitinases of the avian malaria parasite *Plasmodium gallinaceum*, a class of enzymes necessary for parasite invasion of the mosquito midgut, *J.Biol.Chem.*, 275, 10331-10341 (2000), and Y.-L. Tsai, R. E. Hayward, R. C. Langer, D. A. Fidock, and J. M. Vinetz, Disruption of *Plasmodium falciparum* chitinase markedly impairs parasite invasion of mosuito midgut, *Infect.Immun.*, 69, 4048-4054 (2001)] and insects [S. Sakuda, A. Isogai, S. Matsumoto, A. Suzuki, and K. Koseki, The structure of allosamidin, a novel insect chitinase inhibitor produced by Streptomyces sp, *Tetrahedron Lett.*, 27, 2475-2478 (1986); E. Cohen, Chitin synthesis and degradation as targets for pesticide action, *Arch. insect Biochem. Physiol.*, 22, 245-261 (1993); K. Shiomi, N. Arai, Y. Iwai, A. Turberg, H. Koelbl, and S. Omura, Structure of argifin, a new chitinase inhibitor produced by *Gliocladiun* sp., *Tetrahedron Lett.*, 41, 2141-2143 (2000); and N. Arai, K. Shiomi, Y Yamaguchi, R. Masuma, Y. wai, A. Turberg, H. Koelbl, and S. Omura, Argadin, a new chitinase inhibitor, produced by *Clonostachys* sp. FO-7314, *Chem.Pharm.Bull.*, 48, 1442-1446 (2000)].

In addition, a recent study has shown that inhibition of a mammalian chitinase associated with parasitic infections reduces recruitment of inflammatory cells and profoundly dampens T helper 2 (Th2) cellular responses in a murine model of lung inflammation, suggesting this enzyme may be a potential target for an asthma drug therapy [Z. Zhu, T. Zheng, R. J. Horner, Y. K. Kim, N.Y. Chen, L. Cohn, Q. Hamid, and J. A. Elias, Acidic mammalian chitinase in asthmatic Th2 inflammation and IL-13 pathway activation, *Science*, 304, 1678-1682 (2004)].

Furthermore, chitinase-like lectins (chilectins), which are not enzymatically active appear to play a role in carbohydrate recognition and inflammation.

The enzymes have a conserved $(\beta/\alpha)_8$ fold, with a surface groove containing exposed aromatic residues, used for binding the chitin substrate. Family 18 chitinases employ an unusual reaction mechanism, where the acid protonating the glycosidic bond is a conserved glutamate and the nucleophile is the oxygen of the N-acetyl group on the −1 sugar, forming an oxazolinium ion intermediate. A range of chitinase inhibitors have been described, most of which are natural products. Allosamidin is a pseudotrisaccharide that mimics the oxazolinium reaction intermediate, inhibiting family 18 chitinases in the nM-μM range. Argifin, argadin and CI-4 are peptide-based inhibitors that mimic protein-carbohydrate interactions both in terms of hydrogen bonds and stacking interactions. Unfortunately, the currently available inhibitors have a number of properties that make them unsuitable as drug leads, including high molecular weights (e.g. allosamidin, argifin and argadini, several stereocenters, and low cLogP values (e.g. −5.2 for allosamidin). Additionally, such inhibitors are generally large, hydrophilic molecules which contain easily hydrolyzable chemical bonds, and are undesirable for therapeutic uses.

Therefore, there is a need to avoid or overcome the above mentioned disadvantages and provide molecules appropriate for therapy which interact with chitinase enzymes and/or chilectins.

There is also a need to provide molecules for the treatment of diseases such as pathogenic infections involving the synthesis and/or degradation of chitin.

There is also a need to provide molecules for use as anti-pathogenics, such as anti-fungal and anti-parasitic molecules.

There is also a need to provide molecules for use as insecticides.

There is also a need to provide molecules for the prevention or treatment of inflammatory disease.

There is also a need to provide molecules for the treatment of atherosclerosis and lipid storage disease.

Accordingly, the present invention seeks to meet one or more of the present needs.

SUMMARY OF THE INVENTION

According to a first aspect of the present invention there is provided a compound according to formula (I):

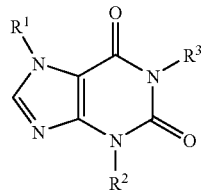

(I)

wherein, $R^1$ and $R^2$ are each independently selected from the group consisting of H, branched or unbranched substituted or unsubstituted alkyl, branched or unbranched substituted or unsubstituted alkenyl, branched or unbranched substituted or unsubstituted alkynyl, carboxy or alkyloxycarbonyl, $R^3$ is a group of formula (II):

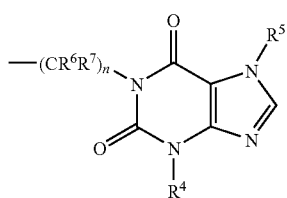

(II)

wherein $R^4$ has the same definition as that given for $R^2$ herein, $R^5$ has the same definition as that given for $R^1$ herein, $R^6$ and $R^7$ are each, at each occurrence, independently selected from H, branched or unbranched substituted or unsubstituted alkyl, branched or unbranched substituted or unsubstituted alkenyl, branched or unbranched substituted or unsubstituted alkynyl, carboxy, alkyloxycarbonyl hydroxyl, amino, nitro, alkyloxy, alkylthio, formyl, cyano, carbamoyl, halo (e.g. fluoro, chloro, bromo or iodo), a ketone or, independently, $R^6$ and $R^7$ may, independently at each occurrence, together form a carbonyl or a $=CH_2$ group, and n is 1, 2, 3, 4 or 5, and excluding the compounds having the formula (IV):

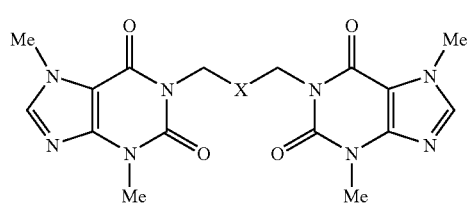

(IV)

wherein $X=-CH(OH)-$ or $-CH(OAc)-$ or $X=-CH(R)-CH(R)-$, wherein R is Br, OH or OAc; and excluding the compounds having the formula (V):

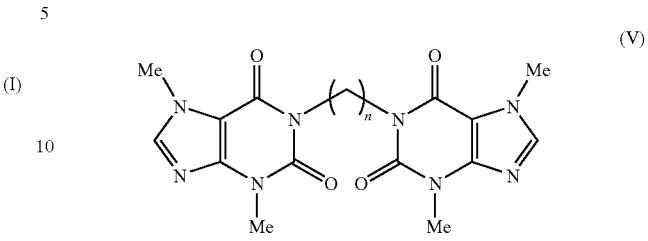

(V)

wherein n=1, 2, 3, 4 or 5.

Chitinase enzymes are found in many organisms, e.g. mammals and pathogenic organisms, and includes a group known as family 18 chitinases. For example, chitinase AfChiB1 is a chitinase found in the fungal pathogen *Aspergillus fumigatus*. Mammalian chitinases include chitotriosidase and acidic mammalian chitinase (AMCase) and the non-enzymatically active family 18 chitinase-like lectins (chilectins) such as HCgp-39, YM-1 and YM-2 which have been implicated in the pathophysiology of inflammation. Thus, the present invention as described herein is applicable to diseases, conditions or other circumstances in which the above-mentioned chitinases are utilised and/or have an activity. Accordingly, such diseases may be described as being associated with a chitinase activity. In particular the molecules described herein may interact with or disrupt chitinase enzymes or chitinase-like lectins in order to treat diseases associated with such chitinases or chitinase-like lectins. For example, the chitinase enzymes may be inhibited by such molecules binding to the enzyme.

Without wishing to be bound by theory, the usefulness of the molecules described herein is believed to be related to the ability of those molecules to bind an active site in the chitinase enzyme. A library of known compounds was screened against the family 18 chitinase, AfChiB1 from the fungal pathogen *Aspergillus fumigatus*, and three known compounds, theophylline, caffeine and pentoxifylline were found to be potent inhibitors of that enzyme. those compounds contain a 1,3-dimethylxanthine substructure. Crystals of the enzyme-inhibitor complexes were prepared and the geometry of the enzyme active site region, including the arrangement of the inhibitor molecule binding in that region was elucidated using x-ray crystallography. From those results, further inhibitor compound structures, based on a di-caffeine type structure, were considered as potential inhibitor molecules for binding the enzyme active site.

Diseases associated with chitinase activity which may be prevented or treated with the compounds described herein include inflammatory or allergic diseases or conditions, such as asthma, hypersensitivity of the lung and lung inflammation, allergic reactions, autoimmune disease, atherosclerosis Or Gaucher's lipid storage disease.

Typical diseases associated with the immune system and which may be treated with the compounds of the present invention include prototypical autoimmune inflammatory diseases.

The diseases include type 1 diabetes melitus, rheumatoid arthritis, psoriasis, systemic lupus erythrematosus (SLE), multiple sclerosis, autoimmune hepatitis, sarcoldosis, inflammatory bowel disease and chronic obstructive pulmonary disease.

Accordingly, according to a second aspect of the present invention, there is provided a compound according to formula (I) as described hereinbefore for use as a medicament.

According to a third aspect of the present invention, there is provided use of a compound according to formula (I) as described hereinbefore for the preparation of a medicament for the prevention or treatment of a disease associated with a chitinase activity.

According to a fourth aspect of the present invention, there is provided use of a compound according to formula (I) as described hereinbefore, for the preparation of a medicament for the prevention or treatment of a disease associated with inflammation.

According to a fifth aspect of the present invention there is provided use of a compound according to formula (III):

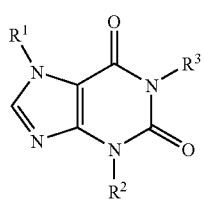

(III)

wherein, $R^1$, $R^2$ and $R^3$ are each independently selected from the group consisting of H, branched or unbranched substituted or unsubstituted alkyl, branched or unbranched substituted or unsubstituted alkenyl, branched or unbranched substituted or unsubstituted alkynyl, carboxy or alkyloxycarbonyl, or $R^3$ is a group of formula (II):

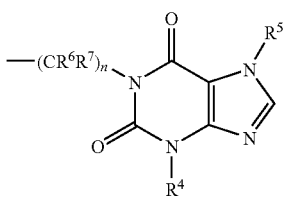

(II)

wherein, $R^4$ has the same definition as that given for $R^2$ herein, $R^5$ has the same definition as that given for $R^1$ herein, $R^6$ and $R^7$ are each, at each occurrence, independently selected from H, branched or unbranched substituted or unsubstituted alkyl, branched or unbranched substituted or unsubstituted alkenyl, branched or unbranched substituted or unsubstituted alkynyl, carboxy, alkyloxycarbonyl hydroxyl, amino, nitro, alkyloxy, alkylthio, formyl, cyano, carbamoyl, halo (e.g. fluoro, chloro, bromo or iodo), a ketone or, independently, $R^6$ and $R^7$ may, independently at each occurrence, together form a carbonyl or a $=CH_2$ group, and n is 1, 2, 3, 4 or 5, for the preparation of a medicament for the prevention or treatment of a pathogenic disease associated with a chitinase activity.

According to a sixth aspect of the present invention, there is provided use of a compound according to formula (III) as described hereinbefore, for the preparation of a medicament for the prevention or treatment of a disease associated with the synthesis or degradation of chitin.

According to a seventh aspect of the present invention, there is provided use of a compound according to formula (III) as described hereinbefore as a fungicide and/or insecticide and/or herbicide.

Pathogenic diseases which may be prevented or treated with the compounds according to formula (III) described herein may be diseases such as fungal infections, for example yeast infections, thrush e.g. oral thrush, farmers lung e.g. caused by the fungus *Aspergillus*, althlete's foot, ringworm, or fungal infections associated with HIV/AIDS.

Other pathogenic diseases include parasitic diseases or infestations caused by ticks or other arachnid infestations, parasitic nematodes, parasitic insects, or protozoa, e.g. malaria which is caused by the protozoan *Plasmodium*.

Fungal infections, and insect infestations occurring in other circumstances may also be treated with the compounds according to formula (III) described hereinbefore, for example mildew, fungal rot, fly infestations and aphids affecting plants, such as food plants and crops, e.g. cereal crops.

In the compound formulae described herein, an alkyl group may be independently a $C_1$-$C_{22}$ alkyl, preferably a $C_1$-$C_{10}$ alkyl, preferably $C_1$-$C_4$ alkyl.

An alkenyl group may be independently a $C_2$-$C_{22}$ alkenyl, preferably a $C_2$-$C_{10}$ alkenyl, preferably $C_2$-$C_4$ alkenyl.

An alkynyl group may be independently a $C_2$-$C_{22}$ alkynyl, preferably a $C_2$-$C_{10}$ alkynyl, preferably $C_2$-$C_4$ alkynyl.

The alkyl, alkenyl or alkynyl groups may be branched or unbranched, substituted or unsubstituted.

As described herein, the alkyl, alkenyl or alkynyl groups may be substituted, and the substituents may be any chemical moiety such as a hydroxyl, substituted or unsubstituted amine, substituted (or unsubstituted amide, halide (such as fluoro, chloro, bromo, iodo), alkoxy, thio, nitro, carboxy, an ester, cyano, or aryl (such as phenyl, naphyl and pyridyl).

Preferably, $R^1$ and $R^2$ in formulae (I) or (III) are independently selected from H, branched or unbranched substituted or unsubstituted alkyl, branched or unbranched substituted or unsubstituted alkenyl.

If substituted, preferable substituents of the alkyl or alkenyl groups may be chosen from hydroxyl, amine, carboxy or ester.

For example, preferably, $R^1$ is independently selected from H, branched or unbranched substituted or unsubstituted alkyl (e.g. $C_1$-$C_{10}$ alkyl, preferably $C_1$-$C_4$ alkyl, most preferably methyl), $CH_2OH$, $CH_2CH_2CO_2Me$, $CH_2$ $(CH_2)_2CO_2Me$, $CH_2$ $(CH_2)_3CO_2Me$, $CH_2CH_2CO_2H$, $CH_2$ $(CH_2)_2CO_2H$, $CH_2$ $(CH_2)_3CO_2H$, $CH_2CH=CHCO_2Me$ (cis- or trans-), or $CH_2CH=CHCO_2H$ (cis- or trans-).

The groups $CH_2CH=CHCO_2Me$ or $CH_2CH=CHCO_2H$ may be in the cis- or trans-geometry, and are most preferably in the cis-geometry.

Preferably, $R^2$ is independently selected from H, branched or unbranched substituted or unsubstituted alkyl (e.g. $C_1$-$C_{10}$ alkyl, preferably $C_1$-$C_4$ alkyl, most preferably methyl), $CH_2OH$, ethyl, iso-propyl, $CH_2CH=CH_2$, $CH_2CH_2NH_2$, $CH_2CH_2OH$, $CH_2CH_2CH_2NH_2$, or $CH_2CH_2CH_2OH$.

For use of a compound according to the math aspect of the present invention preferably $R^1$ and $R^2$ in formula (III) are independently selected from branched or unbranched substituted or unsubstituted alkyl (e.g. $C_1$-$C_{10}$ alkyl, preferably $C_1$-$C_4$ alkyl, most preferably methyl). For use of a compound according to the fifth aspect of the present invention preferably the group, $R^3$ in formula (III), is independently selected from H or branched or unbranched substituted or unsubstituted alkyl e.g. $C_1$-$C_{10}$ alkyl, preferably methyl or $CH_3C(O)(CH_2)_4—$.

A preferred representative compound of formula (I) or (III) is one in which $R^1$ is methyl, $R^2$ is methyl and $R^3$ is $CH_3C(O)(CH_2)_4$—, and this compound is known as pentoxifylline.

Another preferred representative compound of formula (I) or (III) is one in which $R^1$ is hydrogen, $R^2$ is methyl and $R^3$ is methyl, and this compound is known as theophylline.

Another preferred representative compound of formula (I) or (III) is one in which $R^1$ is hydrogen, $R^2$ is hydrogen and $R^3$ is hydrogen, and this compound is known as xanthine.

Another preferred representative compound of formula (I) or (III) is one in which $R^1$ is methyl, $R^2$ is methyl and $R^3$ is methyl, and this compound is known as caffeine.

In the present invention according to any one of the first to seventh aspects, preferably, in the compound of formula (I) or (III), the group $R^3$ is the group of formula (II).

Preferably the value of n is 3.

Preferably, the compound of formula (I) (excluding the compounds of formulae (IV) and (V)) or the compound of formula (III), according to any of the first to seventh aspects is represented by a compound having the following formula (VI):

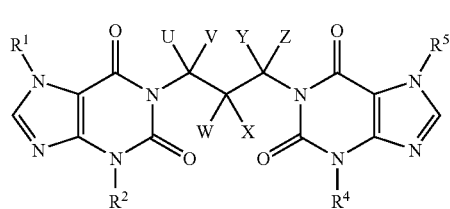

(VI)

In the compound of formula (VI), preferably each of $R^1$ and $R^2$ are as described hereinbefore.

Preferably, $R^1$ and $R^2$ are independently selected from branched or unbranched substituted or unsubstituted alkyl (e.g. $C_1$-$C_{10}$ alkyl, preferably $C_1$-$C_4$ alkyl, most preferably methyl).

$R^4$ and $R^5$ are as defined hereinbefore, and are preferably independently selected from branched or unbranched substituted or unsubstituted alkyl (e.g. $C_1$-$C_{10}$ alkyl, preferably $C_1$-$C_4$ alkyl, most preferably methyl).

It is preferred that U, V, W, X, Y and Z are independently selected from H, OH, an alkyl group as defined hereinbefore, or alkyloxycarbonyl, or independently U and V together or W and X together form a carbonyl or a $=CH_2$ group.

Preferably, the alkyl group is a $C_1$-$C_{10}$ alkyl, preferably $C_1$-$C_4$ alkyl, most preferably methyl.

Preferably, the alkyloxycarbonyl group is a methyloxycarbonyl group i.e. —$CO_2Me$.

It is preferred that U, V, W, X, Y and Z are each hydrogen.

A preferred representative compound of the present invention according to the fifth to seventh aspects is one in which, in formula (VI), $R^1$, $R^2$, $R^4$, and $R^5$ are each methyl, and U, V, W, X, Y and Z are each hydrogen.

Further, preferable compounds according to formula (VI) are:

when $R^1$, $R^2$, $R^4$, and $R^5$ are each methyl and Y and Z are both hydrogen:
U is methyl, and V, W and X are each hydrogen,
U, V and W are each hydrogen, and X is OH,
U, V and W are each hydrogen, and X is methyl,
U and V are each hydrogen, and W and X are each methyl,
U and V are each hydrogen, and W and X together form a carbonyl group,
U, V and W are each hydrogen, and X is $CO_2Me$,
U, V and W are each hydrogen, and X is ethyl,
U and V are each hydrogen, and W and X together form a $=CH_2$ group;

when $R^1$, $R^4$, and $R^5$ are each methyl and U, V, W, X, Y and Z are each hydrogen:
$R^2$ is any one of hydrogen, $CH_2OH$—, ethyl, iso-propyl, $CR_2CH=CH_2$, $CH_2CH_2NH_2$, $CH_2CH_2OH$, $CH_2CH_2CH_2NH_2$, or $CH_2CH_2CH_2OH$;

and when $R^2$, $R^4$, and $R^5$ are each methyl and U, V, W, X, Y and Z are each hydrogen:
$R^1$ is any one of hydrogen, $CH_2OH$, $CH_2CH_2CO_2Me$, $CH_2(CH_2)_2CO_2Me$, $CH_2(CH_2)_3CO_2Me$, $CH_2CH_2CO_2H$, $CH_2(CH_2)_2CO_2H$, $CH_2(CH_2)_3CO_2H$, $CH_2CH=CHCO_2Me$ (cis), or $CH_2CH=CHCO_2H$(cis).

The present invention further provides a treatment or prophylaxis of a disease recited herein comprising administering a compound recited herein to a patient in need thereof.

For use according to the present invention, the compounds described herein may be presented as a pharmaceutical formulation, comprising the compound or salt thereof or other physiologically functional derivative thereof, together with one or more pharmaceutically acceptable carriers therefor and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be Conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, iactated Ringer's or fixed oils. Preservatives and other additives may also be present, such as, for example, antimicrobials, antioxidants, chelating agents, inert gases and the like.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredients and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

For use as a fungicide, insecticide or herbicide, the compound or a salt thereof may be applied by any suitable means, either alone or in combination with a suitable carrier. For example the compound or salt thereof may be applied to a surface in need of treatment or to a plant. The compound or salt thereof may be applied in a gaseous, liquid or solid form. A suitable carrier may be chosen from an inert liquid, in which the compound may be dissolved, dispersed or suspended, or a solid carrier, such as dust. A suitable liquid carrier may be an organic liquid, water or an aqueous solution.

Organic solvents which may be used as carriers include hydrocarbons such as hexane, benzene, toluene xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as carriers or emulsions, can be also employed as carriers for the compound.

The compound can be applied as an aerosol, e.g., be dispersing in air by means of a compressed gas such as dichlorodifluoromethane or trichlorofluoromethane and other Freons or propulsive gases, for example.

The compound may also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour, pumice, trinoli, wood flour, walnut shell flour, redwood flour and lignin.

It may be desirable to incorporate a wetting agent in the solid or liquid compositions. The wetting agent can be anionic cationic or nonionic.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g. sodium stearate and potassium oleate, sodium salt of propylnaphthalene sulfonic acid (di-2-ethylhexyl), ester of sodium sulfosuccinic acid, sodium lauryl sulfate sodium stearate and potassium oleate, sodium salt of the sulfonated monoglyceride or coconut fatty acids, sorbitan, sesquileate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleyltaurate, Turkey Red oil, sodium dibutylnaphthalene sulfonate, sodium lignin sulfonate (Marasperse N), polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1,000), sorbitan sesquioleate, polyethylene glycol ester of tall oil acids, sodium octyl phenoxyethoxyethyl sulfate, polyoxyethylene (20) sorbitan monolaurate ("Tween 20") tris(polyoxyethylene) sorbitan monostearate ("Tween 60"), and sodium dihexyl sulfosuccinate.

The solid, liquid and gaseous formulations can be prepared by any suitable means. For example, the active compound may be tumbled together with finely divided solid carrier. Alternatively, the active compound in liquid form, including solutions, dispersions, emulsions and suspensions thereof, may be admixed with a solid carrier in finely divided form.

Compounds encompassed by formulae (I) or (III) may be prepared by reacting a compound of formula (IX) and/or (X):

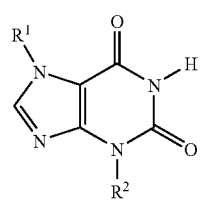

(IX)

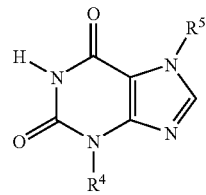

(X)

with a compound of formula (XI):

(XI)

in which $R^1$, $R^2$, $R^4$, $R^5$, $R^6$ and $R^7$ are as defined hereinbefore, and L is at each occurrence independently selected from halogen such as Cl, Br or I, or a leaving group such as tosyl i.e. OTs.

The reaction may proceed for example with a base and in a solvent in anhydrous conditions.

The base may be brought in to contact with a compound of formulae (IX) and/or (X) before introducing the compound of formula (XI).

The reaction temperature may be from about room temperature, e.g. 20° C., to 150° C. For example, the reaction temperature may be from 40° C. to 120° C.

A suitable solvent is dimethylformamide.

The length of time for the reaction to proceed may depend on the particular ingredients and conditions used, but may typically proceed for up to about 24 hours.

The base may be reacted with a compound of formula (IX) and/or (X) for up to about 1 hour before introducing the compound of formula (XI), whereupon the reaction may then proceed for up to about 24 hours, e.g. from 1 to 18 hours.

Alternatively, substituted compounds encompassed by formulae (I) or (III) may be prepared by forming a salt compound according to formula (XII):

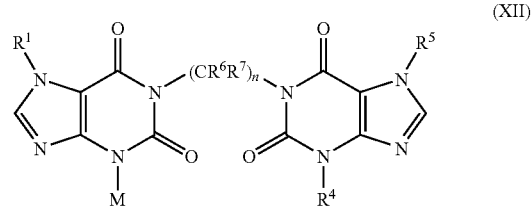

(XII)

wherein, $R^1$, $R^4$, $R^5$, $R^6$ and $R^7$ are as defined hereinbefore, and M is a metal such as an alkali metal, e.g. potassium, which may then be further reacted to introduce a chosen $R^2$ group in place of M by reaction with an $R^2$ halide, i.e. $R^2$Hal.

As an alternative substituted compounds encompassed by formulae (I) or (III) may be prepared by forming a salt compound according to formula (XIII):

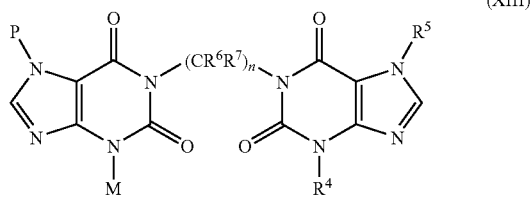

(XIII)

wherein, $R^4$, $R^5$, $R^6$ and $R^7$ are as defined hereinbefore, M is a metal such as an alkali metal, e.g. potassium and P is a protecting group, which may then be further reacted to introduce a chosen $R^1$ in place of P and a chosen $R^2$ group in place of M, e.g. first by reaction with an $R^2$ halide, i.e. $R^2$Hal, to replace M with $R^2$, and then removal of group P, and reaction with an $R^1$ halide, i.e. $R^1$Hal to replace P with $R^1$.

The present invention will now be described with reference to the following non-limiting examples.

BRIEF DESCRIPTION OF DRAWINGS

The present invention will now be described with reference to the following drawings in which.

DETAILED DESCRIPTION

Materials and Methods

Figure 1:
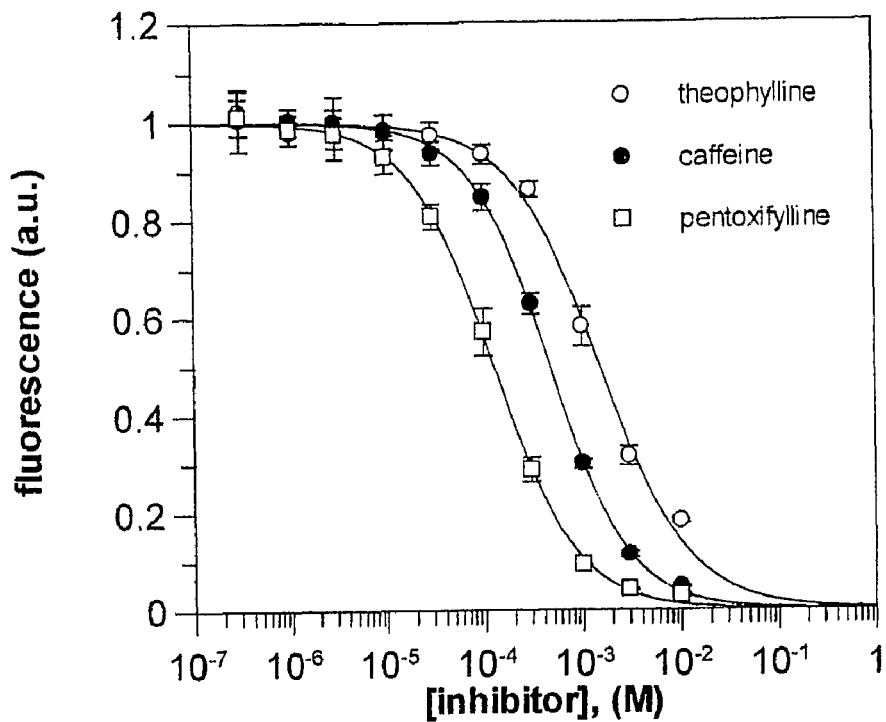
FIG. 1 is a dose response curve for the three inhibitor compounds theophylline, pentoxifylline, and caffeine.

AfChiB1 was expressed, purified and inhibition studies performed as previously described [F. V. Rao, D. R. Houston, R. G. Boot, J. M. F. G. Aerts, M. Hodkinson, D. J. Adams, K. Shiomi, S. Omura, and D. M. F. van Aalten, Specificity and affinity of natural product cyclopentapeptide inhibitors against Aspergillus fumigatus, human and bacterial chitinases, Chemistry & Biology, 12, 65-76 (2005)].

Briefly, AfChiB1 was overexpressed as a GST-fusion protein in E. coli and purified using a combination of affinity and size-exclusion chromatography.

Inhibition studies were also performed on human chitotriosidase and AMCase.

Additionally, for comparison, inhibition studies were performed on celluase from Aspergillus niger, phosphodiesterase 4A and lysozyme.

AfChiB1 Enzymology:

AfChiB1 inhibition was studied using the fluorogenic substrate 4-methylumbelliferyl-β-D-N,N'-diacetylchitobiose (4MU-GlcNAc$_2$; Sigima). Briefly, in a final volume of 50 µl, 2 nM of enzyme was incubated with 20 µM substrate in McIlvain buffer (100 mM citric acid, 200 mM sodium phosphate, pH 5.5) containing 0.1 mg/ml BSA, for 10 min at 37° C. in the presence of different concentration of inhibitors. After the addition of 25 µl of 3 M glycine-NaOH, pH 10.3, the fluorescence of the liberated 4-methylumbelliferone (4MU) was quantified using a Flx 800 microtitrepiate fluorescence reader (Bio-Tek Instruments Inc.), with excitation and emission wavelengths of 360 nm and 460 nm, respectively, using 40 nm slits. Experiments were performed in triplicate. Production of 4MU was linear with time for the incubation period used, and less than 10% of available substrate was hydrolyzed.

AfChiB1 was screened against a small molecule library of 880 compounds (Prestwick Chemical Inc., France). The library was screened with 50 µl assay volumes in 96-well plates, using 2 nM of enzyme, 0.1 mg/ml BSA and 20 µM of substrate and 100 µM inhibitor assuming a compound molecular weight of 500 Da. False positives were removed by monitoring absorbance at the excitation wavelength (360 nm).

For the determination of the mode of inhibition of pentoxifylline, reactions followed the same protocol, using 5-30 µM substrate, its the presence of increasing amounts of the inhibitor. The mode of action was determined by plotting the data as Lineweaver-Burk plots, and by fitting all data to the standard competitive inhibition equation with the GraFit software [R. J. Leatherbarrow, GraFit Version 5, Erithacus Software Ltd., Horley, U.K., (2001)].

Human Chitotriosidase and AMCase:

Gene sequences for the human chitotriosidase and AMCase are known [R. G. Boot, G. H. Renkema, A. Strijland, A. J. van Zonneveld, and J. M. F. G. Aerts, Cloning of a cDNA-encoding chitotriosidase, a human chitinase produced by macrophages, J. Biol. Chem., 270, 26252-26256 (1995); and R. G. Boot, E. F. C. Blommaart, E. Swart, K. Ghauharali van der Vlugt, N. Bijl, C. Moe, A. Place, and J. M. F. G. Aerts, Identification of a novel acidic mammalian chitinase distinct from chitotriosidase, J.Biol.Chem., 276, 6770-6778 (2001)].

cDNAs encoding human chitotriosidase and human AMCase were generated from total human lung RNA using RT PCR and primers based on the published sequence (primer pairs: 5'-gccaccatggtgcggtctgtggcctgggcaggtttc-3' (SEQ ID NO:1) and 5'-tcaattccaggtgcagcatttgcaggagttgctg-3' (SEQ ID NO:2) for chitotriosidase: 5'-gccaccatgacaaagcttat-tctcctcacaggtcttg-3' (SEQ ID NO:3) and 5'-ttatgcccagttgcag-caatcacagctggtgtcgaag-3' (SEQ ID NO:4)for AMCase), then subcloned into p3xFLAG-CMV-13 vector (Sigma chemical Co. St. Louis, Mo., USA). The vector encodes three adjacent FLAG epitopes downstream of the cloning region. Plasmids encoding Flag tagged chitotriosidase and hAMCase were then transiently transfected into HEK 293 cells and supernatants harvested 3 or 6 days after transfection. FLAG-tagged expressing proteins were purified over an anti-FLAG M2 gel affinity column and eluted with a 3XFLAG peptide according to the manufacturers instructions. Inhibitor potencies were determined for the purified proteins using the chitinase assay similar to the one described above. Briefly, the assay consisted of fluorogenic substrate 4-methylumbelliferyl-β-D-N, N'-diacetylchitobiose (4MU-GlcNAc2; Sigma) at a final concentration of 22 µM, along with 1 nM of enzyme in a final volume of 100 µl. The fluorescence was read using excitation and emission wavelengths of 355 nm and 460 nm respectively. The buffers were same as described above for fungal chitinase assessments except that the assay was carried out at 30° C. for 30 minutes.

Cellulase from Aspergillus niger:

Commercially available cellulose from Aspergillus niger (Sigma: C-1184) was assayed, using the fluorogenic substrate 4-methylumbelliferyl-β-D-cellobioside (Sigma M-6018). In a final volume of 50 µl, 5 nM of enzyme was incubated with 20 µM substrate in McIlvain buffer containing 0.1 mg/ml BSA, for 30 min at 37° C. in the presence of different concentration of inhibitors. After the addition of 25 µl of 3 M glycine-NaOH, pH 10.3, the fluorescence of the liberated 4-methylumbelliferone (4MU) was quantified using an Flx 800 microtitreplate fluorescence reader (Bio-Tek Instruments Inc.), with excitation and emission wavelengths of 360 nm and 460 mL, respectively, using 40 nm slits. Experiments were performed in triplicate. Production of 4MU was linear with time for the incubation period used, and less than 10% of available substrate was hydrolyzed.

Phosphodiesterase 4A (PDE4A):

Phosphodiesterase 4A (PDE4A) was assayed using a Sf9 expressed GST-fusion and activity was monitored by hydrolysis of [$^3$H]cAMP to [$^3$H]AMP using the PDE-SPA kit from Amersham Pharmacia Biotech as described previously [31]. The assay reaction contained 100 nM [$^3$H]cAMP (1 µCi/ml) in a buffer containing 20 mM HEPES (pH 7.5), 10 mM MgCl$_2$, 100 mM EDTA, 100 mM KCl and 2 µl of test compound in DMSO at 30° C. The reaction was initiated by addition of enzyme for 10 min. The potency of inhibitors (IC$_{50}$) was determined from a dose-response curve. Experiments were performed with n=6.

Lysozyme:

Lysozyme was assayed using the EnzCheck Lysozyme kit from Molecular probes as described by the manufacturer. Chicken egg white lysozyme and its substrate, fluorescein labeled *Micrococcus lysodeikyius* cell wall (DQ Lysozyme substrate) were used to determine compound inhibition. Briefly, 6.25 units of lysozyme were incubated with 25 µg of DQ substrate with or without various concentrations of inhibitor in a total volume of 100 µl at 37° C. for 30 minutes. The fluorescence was determined using excitation and emission wavelengths of 360 nm and 460 nm, respectively. The potency of inhibitors (IC$_{50}$) was determined from a dose-response curve. Experiments were performed in triplicate.

Results

Inhibitor Screening:

A commercially available library of 880 drug molecules was screened at 100 µM against a family 18 chitinase, chitinase B1 from *A. fumigatus* (AfChiB1), using a fluorescent assay. From this screen, two methyl xanthine derivatives, theophylline and pentoxifylline, were identified, possessing a common 1,3-dimethylxanthine substructure. Inhibition by theophylline and pentoxifylline, and the closely related methyl xanthine caffeine, was initially confirmed by dose response curves (FIG. 1), with IC$_{50}$'s ranging from 1500 µM (theophylline) to 126 µM (pentoxifylline) in Table I. Initial enzyme velocity measurements at different concentrations of substrate (5-30 µM) and pentoxifylline (0-60, 50 and 200 µM) were used to demonstrate that pentoxifylline is a competitive inhibitor with a K$_i$ of 37 µM (FIG. 2, Table I).

Humans possess two family 18 chitinases, a chitotriosidase [C. E. M. Hollak, S. van Weely, M. H. J. van Oers, and J. M. F. G. Aerts, Marked elevation of plasma chitotriosidase activity—a novel hallmark of Gaucher disease, *J. Clin. Invest.*, 93, 1288-1292 (1994).] and AMCase, an enzyme with an unusual (acidic pH optimum, whose elaboration in vivo is probably evolutionarily tied to protective anti-parasitic host responses to chitin-bearing pathogens. These enzymes, like AfChiB1, are of the "bacterial" type of family 18 chitinases, possessing a deep catalytic cleft lined with solvent exposed aromatic residues (F. Fusetti, H. von Moeller, D. Houston, H. J. Rozeboom, B. W. Dijkstra, R. G. Boot, J. M. F. G. Aerts, and D. M. F. van Aalten, Structure of human chitotriosidase—implications for specific inhibitor design and function of mammalian chitinase-like lectins, *J.Biol.Chem.*, 277, 25537-25544 (2002)], sharing 31% and 28% sequence identity with AfChiB1, respectively. In agreement with this, the methylxanthines also inhibit the human chitinases, with IC$_{50}$'s up to 98 µM, for pentoxifylline (Table I).

As a comparison, the inhibition of human phosphodiesterase-4 by theophylline, caffeine and pentoxifylline was measured using a PDE-SPA assay, and was barely detectable (Table I). As a further control, inhibitory potential of these xanthine derivatives was tested against two other glycoside hydrolases, lysozyme (using a fluorescein-based assay) and cellulase from *Aspergillus niger* (CAZY family GH 8, using the fluorescent substrate 4-methylumbelliferyl-β-D-cellobioside), showing at most 1 mM inhibition (Table I). Together these data suggest that there may be a specific AfChiB1-pentoxifylline interaction.

TABLE 1

Methylxanthine inhibition/binding of family 18 chitinases, a phosphodiesterase and two control glycoside hydrolases.

|  | theophylline | caffeine | pentoxifylline |
|---|---|---|---|
| AfChiB1 IC$_{50}$ (µM) | 1500 ± 90 | 469 ± 23 | 126 ± 7 (K$_i$ = 37 ± 2) |
| AfChiB1 K$_d$ (µM) | — | — | 43 ± 10 |
| hCHT IC$_{50}$ (µM) | >500 | 257 ± 8 | 98 ± 8 |
| hAMCase activity at 1 mM | 36% | 36% | 49% |
| *A. niger* cellulase IC$_{50}$ (µM) | 1008 ± 159 | 1250 ± 278 | 881 ± 319 |
| Egg white lysozyme activity at 500 µM | 100% | 100% | 100% |
| hPDE-4 activity at 50 µM | 24% | 26% | XXX |

Figure 2:
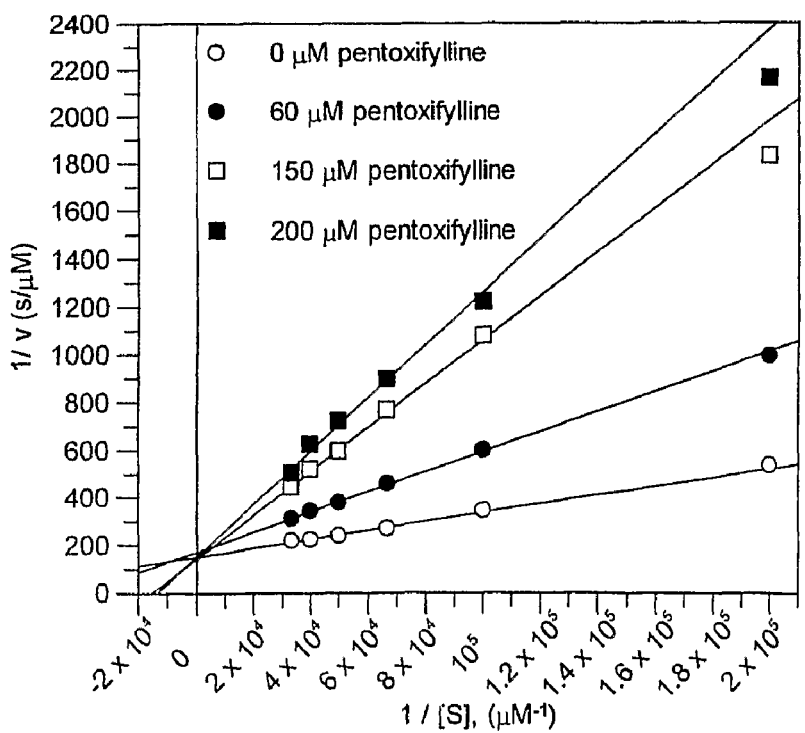
FIG. 2 is graph showing the results of initial enzyme velocity measurements at different concentrations of substrate (5-30 µM) and pentoxifylline (0, 60, 50 and 200 µM) used to demonstrate that pentoxifylline is a competitive inhibitor with a $K_i$ of 37 µM.

IC$_{50}$ were determined as discussed in the text, and as shown for AfChiB1 in FIG. 1. The pentoxifylline K$_i$ was determined by fitting all data shown in FIG. 2 to the standard equation for a competitive inhibitor.

Inhibition Studies on Human and Mouse AMCase and Chitotriosidase

Further inhibition studies were performed using the following compounds: caffeine, theophylline, pentoxifylline and two compounds according to formula (V), wherein, R$^1$, R$^2$, R$^4$, and R$^5$ are each methyl, and U, V, W, X, Y and Z are each hydrogen, and in one compound, n is 0 (Compound (VII)) and in the other compound, n is 1 (Compound (VIII)).

The IC50 results are shown in Table 2, and indicate that the compound according to formula (VIII) is the most potent of the five compounds tested.

TABLE 2

| Compound | H.Chito Trio pH 5.2 | H.Chito Bio pH 5.2 | H.AMCase Bio pH 4.5 | M.AMCase Bio pH 4.5 | M.Chito Bio pH 5.2 |
|---|---|---|---|---|---|
| caffeine | 850 | 650 | 500 | 800 | >1000 |
| theophylline | 1700 | 1750 | ±2000 | ±1600 | >2000 |
| pentoxifylline | 400 | 400 | 400 | 400 | ±1000 |
| Compound (VII) | ±200 | 50-100 | ±1000 |  |  |
| Compound (VIII) | 5-10 | 1 | 10 | 10 | 50-100 |

The compounds according to an embodiment of the present invention were prepared according to the following methods, and further evaluated as inhibitors against AfChiB using the fluorescence-based assay described herein using 4methylumbelliferyl β-D-N,N-deacetyl-chitobioside as substrate. The assay results are shown in the accompanying tables 3-6.

Compounds 1-4 recited herein below were prepared according to the method of Cavalloro et al. (R. A. Cavallaro, L. Filocamo, A. Galuppi, A. Galione, M. Brufani) and A. A. Genazzani, *J. Med. Chem.* 1999, 42, 2527-2534:

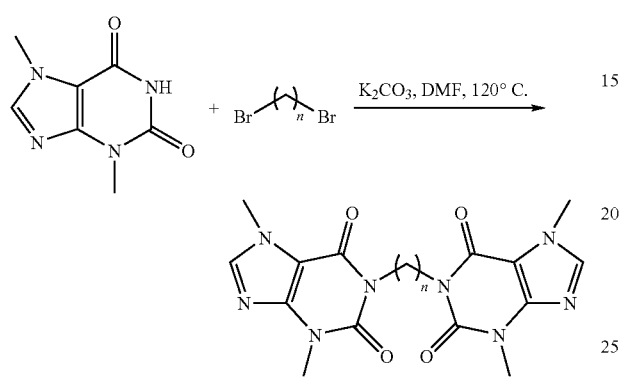

Method: A stirred suspension of theobromine (2 mmol) and anhydrous $K_2CO_3$ (2 mmol) in dry DMF was heated at 120° C. for 1 h, then the appropriate alkyl halide (1.1 mmol) was added dropwise, and the mixture was stirred for 1-18 h. The reaction mixture was cooled at room temperature, $H_2O$ was added, and the mixture was neutralized by adding 0.1 N HCl. The mixture was extracted with $CHCl_3$; after drying over $Na_2SO_4$, the organic layer was evaporated in vacuo to give crude products which were recrystallised from hot MeOH.

TABLE 3

| Compound Number | n | IC$_{50}$(AfChiB) |
|---|---|---|
| 1 | 2 | 6 μM |
| 2 | 3 | 230 nM |
| 3 | 4 | 6 μM |
| 4 | 5 | >10 mM |

Compounds 5-8, recited herein below were also prepared according to the method of Cavalloro et al. For volatile, dihalides, a temperature of 80° C. was employed. The crude products were purified by crystallisation or $SiO_2$ chromatography (MeOH/CHCl$_3$ solvent).

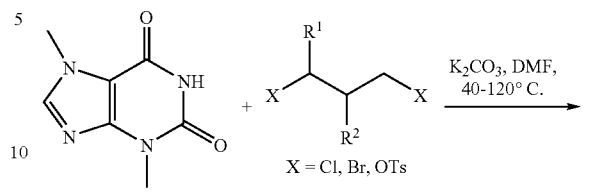

TABLE 4

| Compound Number | R$^1$ | R$^2$ | IC$_{50}$(AfChiB) |
|---|---|---|---|
| 5 | Me | H | 1.1 μM |
| 6 | H | Me | 12 μM |
| 7 | H | OH | 1.4 μM |
| 8 | H | =C | 5.7 μM |

Compounds 9-25, recited herein below were prepared according to a modification of a method described by Zavialov (I. A. Zavialov, V. H. Dahanukar, H. Nguyen, C. Orr, F Zhang and D. R. Andrews, *Org. Lett.*, 2004, 6, 3017), and which is depicted in the following schemes. The intermediate compound A was formed as a crude salt which was used directly in further reaction without further purification.

Alternatively, the compounds maybe prepared according to a modification of the method of Zavaliov et al. (I. A. Zavialov, V. H. Dahanukar, H. Nguyen, C. Orr and D. R. Andrews, *Org. Lett.* 2004, 6, 2237-2240) wherein theobromine or another xanthine is alkylated on N1 with a urethane-protected bromoalkylamine according to the general procedure of Cavallaro. The resulting substituted urethane derivative is then combined with a protected 4-amino-5-alkoxycarbonylimidazole by analogy with Zavialov to generate an orthogonally functionalised dicaffeine which may then be selectively derivatised at the N3/N7 (N3'/N7') positions.

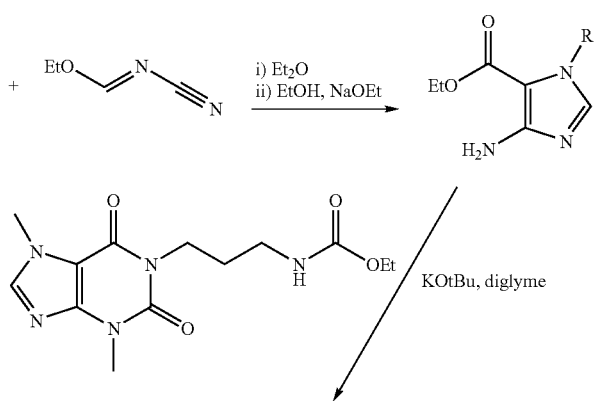

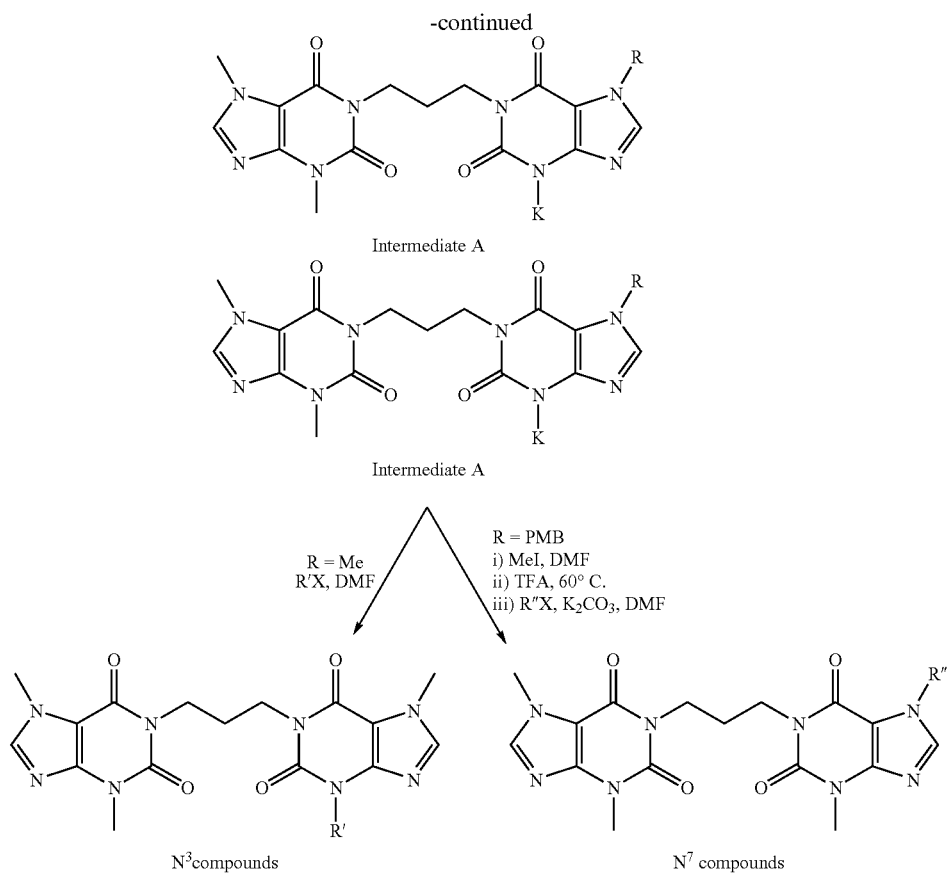

Intermediate A

Intermediate A

R = Me
R'X, DMF

R = PMB
i) MeI, DMF
ii) TFA, 60° C.
iii) R''X, K$_2$CO$_3$, DMF

N$^3$ compounds

N$^7$ compounds

TABLE 5

N$^3$ compounds:

| Compound Number | R' | IC$_{50}$ |
|---|---|---|
| 9 | H | 86 nM |
| 10 | Et | 310 nM |
| 11 | Allyl | 140 nM |
| 12 | iPr | 520 nM |
| 13 | EtNH$_2$ | 78 nM |
| 14 | EtOH | 180 nM |
| 15 | PrNH$_2$ | 440 nM |
| 16 | PrOH | 440 nM |

TABLE 6

N$^7$ compounds:

| Compound Number | R'' | IC$_{50}$ |
|---|---|---|
| 17 | H | 200 nM |
| 18 | EtCOOMe | 93 nM |
| 19 | EtCO$_2$H | 160 nM |
| 20 | PrCO$_2$Me | 140 nM |
| 21 | PrCOOH | 200 nM |
| 22 | BuCO$_2$Me | 300 nM |
| 23 | BuCO$_2$H | 360 nM |
| 24 | CH$_2$CH=CHCO$_2$Me | 160 nM |
| 25 | CH$_2$CH=CHCO$_2$H | 420 nM |

---

The invention claimed is:

1. A compound according to formula (I):

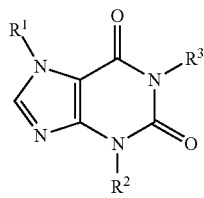

wherein, $R^1$ and $R^2$ are each independently selected from the group consisting of H, branched or unbranched substituted or unsubstituted alkyl, branched or unbranched substituted or unsubstituted alkenyl, branched or unbranched substituted or unsubstituted alkynyl, carboxy and alkyloxycarbonyl, $R^3$ is a group of formula (II):

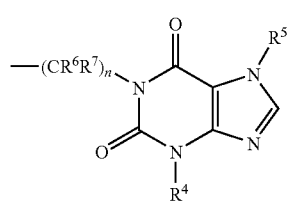

wherein, $R^4$ has the same definition as that given for $R^2$ herein, $R^5$ has the same definition as that given for $R^1$ herein, $R^6$ and $R^7$ are each, at each occurrence, independently selected from the group consisting of H, branched or unbranched substituted or unsubstituted alkyl, branched or unbranched substituted or unsubstituted alkenyl, branched or unbranched substituted or unsubstituted alkynyl, carboxy, alkyloxycarbonyl, hydroxyl, amino, nitro, alkyloxy, alkylthio, formyl, cyano, carbamoyl and halo, or, independently, $R^6$ and $R^7$ may, independently at each occurrence, together form a $=CH_2$ group, and n is 1, 2, 3, 4 or 5, with the proviso that if n is 1, $R^6$ and $R^7$ are independently selected from the group consisting of H, branched or unbranched substituted or unsubstituted alkyl, branched or unbranched substituted or unsubstituted alkenyl, branched or unbranched substituted or unsubstituted alkynyl, carboxy, alkyloxycarbonyl, hydroxyl, amino, nitro, alkyloxy, alkylthio, formyl, cyano, carbamoyl and halo, or, $R^6$ and $R^7$ may, together form a $=CH_2$ group, and excluding the compounds having the formula (IV):

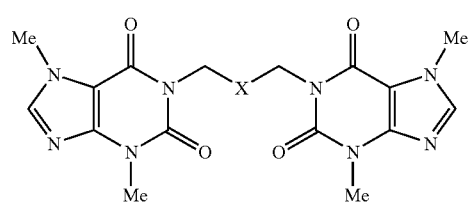

wherein X=—CH(OH)—; or
X=—CH(R)—CH(R)—, wherein R is Br, OH;
and excluding the compounds having the formula (V):

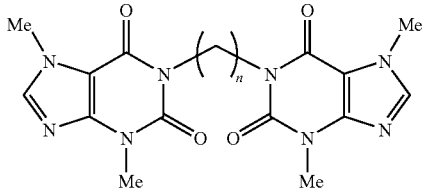

wherein n=1, 2, 3, 4 or 5.

2. The compound according to claim 1, according to formula (VI):

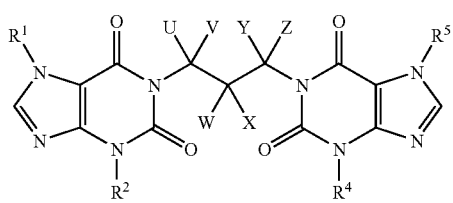

wherein,
R¹ and R² are each independently selected from the group consisting of H, branched or unbranched substituted or unsubstituted alkyl, branched or unbranched substituted or unsubstituted alkenyl, branched or unbranched substituted or unsubstituted alkynyl, carboxy and alkyloxycarbonyl, R⁴ has the same definition as that given for R² herein,
R⁵ has the same definition as that given for R¹ herein, and
U, V, W, X, Y and Z are independently selected from the group consisting of H, OH, a branched or unbranched substituted or unsubstituted alkyl and alkyloxycarbonyl, or, independently U and V together or W and X together form a =CH₂ group.

3. The compound according to claim 2, wherein U, V, W, X, Y and Z are each hydrogen.

4. A pharmaceutical formulation, comprising a compound according to formula (I):

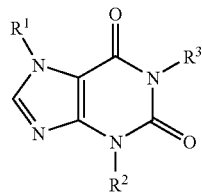

wherein,
R¹ and R² are each independently selected from the group consisting of H, branched or unbranched substituted or unsubstituted alkyl, branched or unbranched substituted or unsubstituted alkenyl, branched or unbranched substituted or unsubstituted alkynyl, carboxy and alkyloxycarbonyl, R³ is a group of formula (II):

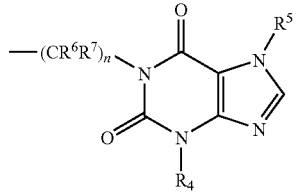

wherein,
R⁴ has the same definition as that given for R² herein,
R⁵ has the same definition as that given for R¹ herein,
R⁶ and R⁷ are each, at each occurrence, independently selected from the group consisting of H, branched or unbranched substituted or unsubstituted alkyl, branched or unbranched substituted or unsubstituted alkenyl, branched or unbranched substituted or unsubstituted alkynyl, carboxy, alkyloxycarbonyl, hydroxyl, amino, nitro, alkyloxy, alkylthio, formyl, cyano, carbamoyl and halo, or, independently,
R⁶ and R⁷ may, independently at each occurrence, together form a =CH₂ group, and
n is 1, 2, 3, 4 or 5, and
excluding the compounds having the formula (IV):

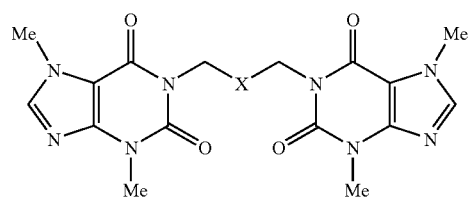

wherein X=—CH(OH)—; or
X=—CH(R)—CH(R)—, wherein R is Br, or OH;
and excluding the compounds having the formula (V):

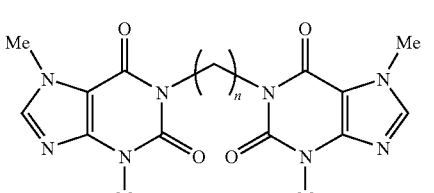

wherein n=1, 2, 3, 4 or 5,
or salts thereof, together with one or more pharmaceutically acceptable carriers therefor.

5. The pharmaceutical formulation of claim 4, comprising a compound according to formula (VI):

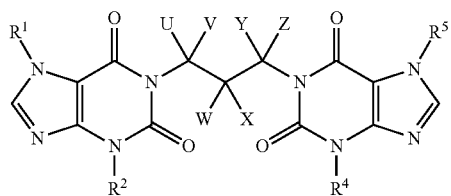

(VI)

wherein,
R$^1$ and R$^2$ are each independently selected from the group consisting of H, branched or unbranched substituted or unsubstituted alkyl, branched or unbranched substituted or unsubstituted alkenyl, branched or unbranched substituted or unsubstituted alkynyl, carboxy and alkyloxycarbonyl, R$^4$ has the same definition as that given for R$^2$ herein, R$^5$ has the same definition as that given for R$^1$ herein, and U, V, W, X, Y and Z are independently selected from the group consisting of H, OH, branched or unbranched substituted or unsubstituted alkyl and alkyloxycarbonyl, or independently U and V together or W and X together form a =CH$_2$ group.

6. The pharmaceutical formulation according to claim 5, wherein U, V, W, X, Y and Z are each hydrogen.

* * * * *

UNITED STATES PATENT AND TRADEMARK OFFICE
CERTIFICATE OF CORRECTION

PATENT NO. : 8,207,175 B2
APPLICATION NO. : 11/922795
DATED : June 26, 2012
INVENTOR(S) : Van Aalten et al.

Page 1 of 2

It is certified that error appears in the above-identified patent and that said Letters Patent is hereby corrected as shown below:

On The Title Page:
Item (57) Abstract: Please correct formula

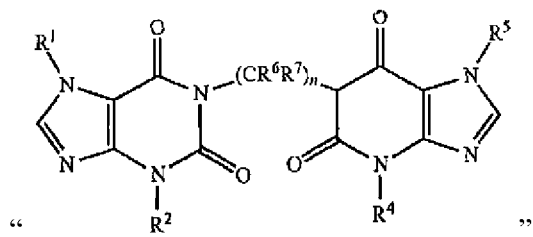

"

to read

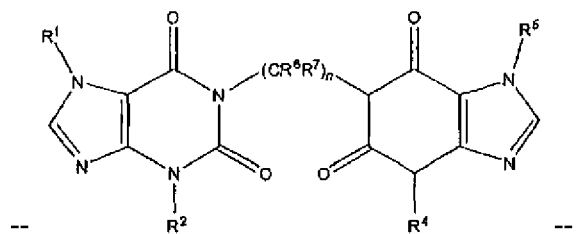

--    --

In The Patent:
Column 1, Line 26: Please insert the title -- INTRODUCTION -- before the text Column 2, Line 18: Please correct "R. J. Horner," to read -- R. J. Homer --

Column 8, Line 7: Please correct "CH₂OH–" to read -- CH₂OH --

Column 15, Line 46: Please correct "(0-60, 50" to read -- (0, 60, 50" --

Signed and Sealed this
Second Day of April, 2013

Teresa Stanek Rea
*Acting Director of the United States Patent and Trademark Office*

CERTIFICATE OF CORRECTION (continued)
U.S. Pat. No. 8,207,175 B2

Column 18, third figure: Please correct

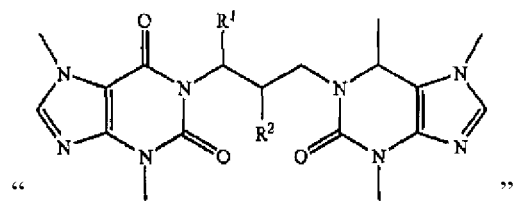

" "

to read

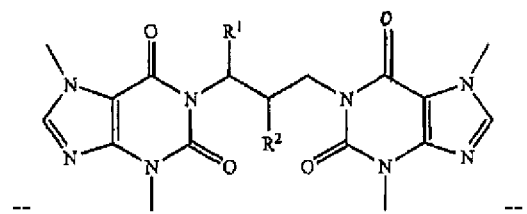

-- --